(12) United States Patent
Kosover et al.

(10) Patent No.: US 7,728,083 B1
(45) Date of Patent: Jun. 1, 2010

(54) AROMATIC SULFONIC ACIDS, AMINES AND NITROPHENOLS IN COMBINATION WITH NITROXYL RADICAL-CONTAINING COMPOUNDS OR C-NITROSOANILINES AS POLYMERIZATION INHIBITORS

(75) Inventors: Vilan Kosover, Cheshire, CT (US); Jesus R. Fabian, New Fairfield, CT (US); Istvan Lippai, Naugatuck, CT (US); Brigitte Benage, Wolcott, CT (US); Gerald J. Abruscato, Southington, CT (US)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 12/694,693

(22) Filed: Jan. 27, 2010

Related U.S. Application Data

(62) Division of application No. 11/170,304, filed on Jun. 28, 2005.

(60) Provisional application No. 60/632,528, filed on Dec. 3, 2004.

(51) Int. Cl.
C08F 2/38 (2006.01)

(52) U.S. Cl. ............................. 526/82; 526/83; 526/84; 526/85

(58) Field of Classification Search .................. 526/82, 526/83, 84, 85
See application file for complete search history.

(56) References Cited

U.S. PATENT DOCUMENTS

| | | | |
|---|---|---|---|
| 2,046,356 A | 7/1936 | Wyler et al. | |
| 2,867,672 A | 1/1959 | Hemmerich | |
| 3,148,225 A | 9/1964 | Albert | |
| 3,163,677 A | 12/1964 | Hoffmann et al. | |
| 3,334,103 A | 8/1967 | Feldman et al. | |
| 3,372,182 A | 3/1968 | Hoffmann et al. | |
| 3,422,144 A | 1/1969 | Hoffmann et al. | |
| 3,494,930 A | 2/1970 | Dupeyre et al. | |
| 3,502,692 A | 3/1970 | Feldman et al. | |
| 3,873,564 A | 3/1975 | Schneider et al. | |
| 3,966,711 A | 6/1976 | Rasberger | |
| 4,053,304 A | 10/1977 | Tsuda | |
| 4,086,147 A | 4/1978 | Watson | |
| 4,468,343 A | 8/1984 | Butler et al. | |
| 4,664,845 A | 5/1987 | Jancis et al. | |
| 4,665,185 A | 5/1987 | Winter et al. | |
| 4,670,131 A | 6/1987 | Ferrell | |
| 5,212,272 A * | 5/1993 | Sargent et al. ............ 526/317.1 |
| 5,254,760 A | 10/1993 | Winter et al. | |
| 5,290,888 A | 3/1994 | Gatechair et al. | |
| 5,446,220 A * | 8/1995 | Arhancet ....................... 585/5 |
| 5,545,782 A | 8/1996 | Winter et al. | |
| 5,545,786 A | 8/1996 | Winter et al. | |
| 5,590,232 A | 12/1996 | Wentworth et al. | |
| 5,648,573 A | 7/1997 | Arhancet et al. | |
| 5,922,244 A | 7/1999 | Koch et al. | |
| 5,932,735 A | 8/1999 | Cunkle et al. | |
| 6,136,951 A | 10/2000 | Benage et al. | |
| 6,143,205 A | 11/2000 | Sutoris et al. | |
| 6,653,414 B2 | 11/2003 | Benage et al. | |
| 6,660,181 B2 | 12/2003 | Benage et al. | |
| 6,685,823 B2 * | 2/2004 | Benage et al. .......... 208/48 AA |
| 7,045,647 B2 | 5/2006 | Benage | |
| 7,473,795 B2 | 1/2009 | Benage | |
| 2004/0147797 A1 | 7/2004 | Tanizaki et al. | |

FOREIGN PATENT DOCUMENTS

| | | |
|---|---|---|
| EP | 0398633 A1 | 11/1990 |
| EP | 0532240 | 3/1993 |
| EP | 0765856 A1 | 4/1997 |
| GB | 1354420 | 6/1974 |
| JP | 6-234700 | 8/1994 |
| JP | 2004300307 | 10/2004 |
| SU | 1027150 | 7/1983 |
| SU | 1139722 | 2/1985 |
| SU | 1558888 | 4/1990 |
| WO | 98/25872 | 6/1998 |
| WO | 02/33026 | 4/2002 |
| WO | 03/070687 | 8/2003 |

OTHER PUBLICATIONS

International Search Report for PCT/US2005/030673 dated Jun. 15, 2006 (4 pages).
International Preliminary Report on Patentability and Written Opinion for PCT/US2005/030673 dated Jun. 5, 2007 (9 pages).

* cited by examiner

*Primary Examiner*—William K Cheung
(74) *Attorney, Agent, or Firm*—JoAnn Villamizar

(57) ABSTRACT

Disclosed herein is a method for inhibiting and retarding the premature polymerization and the polymer growth of vinyl aromatic monomers wherein the method comprises adding to said monomers an effective amount of an inhibitor and retarder blend comprising:
(A) at least one aromatic sulfonic acid;
(B) at least one amine;
(C) at least one nitrophenol; and
(D) at least one member of the group consisting of nitroxy radical-containing compounds and nitrosoanilines.

14 Claims, No Drawings

AROMATIC SULFONIC ACIDS, AMINES AND NITROPHENOLS IN COMBINATION WITH NITROXYL RADICAL-CONTAINING COMPOUNDS OR C-NITROSOANILINES AS POLYMERIZATION INHIBITORS

This application is a divisional of and claims the benefit under Title 35, United States Code, §120 to copending U.S. patent application Ser. No. 11/170,304, filed Jun. 28, 2005, filed Sep. 30, 2005, which claims priority to U.S. Provisional Application No. 60/632,528, filed Dec. 3, 2004, entitled AROMATIC SULFONIC ACIDS, AMINES AND NITROPHENOLS IN COMBINATION WITH NITROXYL RADICAL-CONTAINING COMPOUNDS OR C-NITROSOANILINES AS POLYMERIZATION INHIBITORS. Each of these documents is incorporated herein by reference in its entirety.

BACKGROUND OF THE INVENTION

1. Field of the Invention

The present invention is directed to the inhibition and retardation of the polymerization of vinyl aromatic monomers by means of the addition thereto of combinations of aromatic sulfonic acids, amines, and nitrophenols with nitroxyl radical-containing compounds or C-nitrosoanilines.

2. Description of Related Art

Many ethylenically unsaturated monomers undesirably polymerize at various stages of their manufacture, processing, handling, storage, and use. Polymerization, such as thermal polymerization, during their purification results in the loss of the monomer, i.e., a lower yield, and an increase in the viscosity of any tars that may be produced. The processing and handling of the higher viscosity tars then require higher temperature and work (energy cost) to remove residual monomer.

Polymerization can also result in equipment fouling, especially in the case of production of acrylic monomers. Such polymerization causes loss in production efficiency owing to the deposition of polymer in or on the equipment being used. These deposits must be removed from time to time, leading to additional loss in production of the monomer.

A wide variety of compounds has been proposed and used for inhibiting uncontrolled and undesired polymerization of ethylenically unsaturated monomers. However, many of these compounds have not been fully satisfactory.

U.S. Pat. No. 2,867,672 discloses that the polymerization of uninhibited styrene condensing in liquid form on the surfaces containing the vapor space above the liquid level of the main body of styrene in a tank may be minimized by spraying the surfaces enclosing the vapor space with a styrene polymerization inhibitor.

U.S. Pat. No. 4,086,147 discloses a process for the distillation of readily polymerizable vinyl aromatic compounds comprising subjecting a vinyl aromatic compound to elevated temperatures in a distillation system in the presence of a polymerization inhibitor comprising m-nitro-p-cresol.

U.S. Pat. No. 4,468,343 discloses a compound and a process for utilizing the compound to prevent the polymerization of vinyl aromatic compounds, such as styrene, during heating. The composition includes effective amounts of 2,6-dinitro-p-cresol and either a phenylenediamine or 4-tert-butylcatechol respectively, to act as a polymerization co-inhibitor system in the presence of oxygen.

U.S. Pat. No. 4,670,131 discloses controlling the fouling of equipment used for processing of organic feed streams containing olefinic compounds by inhibiting polymerization of the olefinic compounds by carrying out the processing in the presence of from about 20 ppb to less than 1000 ppb of a stable free radical, such as a nitroxide.

U.S. Pat. No. 5,254,760 discloses the inhibition of the polymerization of a vinyl aromatic compound, such as styrene, during distillation or purification by the presence of at least one stable nitroxyl compound together with at least one aromatic nitro compound.

U.S. Pat. No. 5,290,888 discloses a process for stabilizing an ethylenically unsaturated monomer or oligomer from premature polymerization whereby a stabilizing amount of an N-hydroxy substituted hindered amine is added to said polymerizable monomer or oligomer. The ethylenically unsaturated monomer or oligomer encompass vinyl monomers or oligomers bearing at least one polymerizable moiety. The N-hydroxy substituted hindered amine is said to inhibit premature polymerization in the liquid and/or vapor phase.

U.S. Pat. No. 5,446,220 discloses methods for inhibiting the polymerization of vinyl aromatic monomers in oxygen-free processing systems. These methods comprise adding from 1 to about 10,000 parts per million parts monomer of a combination of a dinitrophenol compound, a hydroxylamine compound and a phenylenediamine compound. Preferably, 2-sec-butyl-4,6-dinitrophenol or 4,6-dinitro-o-cresol are used in combination with bis-(hydroxypropyl)hydroxylamine and N,N'-di-sec-butyl-p-phenylenediamine.

U.S. Pat. No. 5,545,786 discloses that nitroxyl inhibitors in combination with some oxygen reduce the premature polymerization of vinyl aromatic monomers during the manufacturing processes for such monomers. It is also disclosed that even small quantities of air used in combination with the nitroxyl inhibitors result in vastly prolonged inhibition times for said monomers.

U.S. Pat. No. 5,932,735 discloses that selected derivatives of 1-oxyl-2,2,6,6-tetramethyl-4-hydroxypiperidine are effective as inhibitors to prevent the premature polymerization of acrylic and methacrylic acids, their esters, their amides, vinyl acetate and acrylonitrile in the presence of water.

U.S. Pat. No. 6,143,205 discloses a mixture for inhibiting the premature polymerization of monomers that contains (A) vinyl-containing monomers, and (B) an effective amount of a mixture of (i) from 0.05 to 4.5% by weight, based on the total mixture (B), of at least one N-oxyl compound of a secondary amine which carries no hydrogen atoms on the α-carbon atoms and (ii) from 99.95 to 95.5% by weight, based on the total mixture (B), of at least one nitro compound.

Russian patents 1,027,150; 1,139,722; and 1,558,888 disclose decreased polymer formation during normal operating conditions (true inhibitors), but do not protect the system in emergency feed shut off situations, i.e., there is no retarder effect.

The foregoing are incorporated herein by reference in their entirety.

SUMMARY OF THE INVENTION

In accordance with the present invention, it has been found that nitroxyl radical-containing compounds, such as 4-oxo-TEMPO, or C-nitrosoanilines, such as 4-nitroso-N-(1,4-dimethylpentyl)-aniline, are excellent inhibitors and retarders to prevent polymerization of vinyl aromatic compounds when combined with aromatic sulfonic acids, such as dodecylbenzenesulfonic acid (DBSA); amines, such as N-methyl-2-pyrrolidinone (NMP); and nitrophenols, such as 2,4-dinitro-6-sec-butylphenol (DNBP).

It is thus an object of the present invention to develop a highly efficient and inexpensive polymerization inhibitor blend with superb true inhibitor and retarder capabilities.

This and other objects are obtained by the present invention, which is directed to a method for inhibiting and retarding the premature polymerization and the polymer growth of vinyl aromatic monomers comprising adding to said monomers an effective amount of an inhibitor and retarder blend comprising:

(A) at least one aromatic sulfonic acid;
(B) at least one amine;
(C) at least one nitrophenol; and
(D) at least one member of the group consisting of nitroxy radical-containing compounds and nitrosoanilines.

In another embodiment, the present invention is directed to composition comprising a blend of:

(A) at least one aromatic sulfonic acid;
(B) at least one amine;
(C) at least one nitrophenol; and
(D) at least one member of the group consisting of nitroxy radical-containing compounds and nitrosoanilines.

In still another embodiment, the present invention is directed to a composition comprising a vinyl aromatic monomer and a polymerization inhibiting and retarding amount of a blend comprising:

(A) at least one aromatic sulfonic acid;
(B) at least one amine;
(C) at least one nitrophenol; and
(D) at least one member of the group consisting of nitroxy radical-containing compounds and nitrosoanilines.

DESCRIPTION OF THE PREFERRED EMBODIMENTS

As stated above, the present invention is directed to a method for inhibiting and retarding the premature polymerization and the polymer growth of vinyl aromatic monomers comprising adding to said monomers an effective amount of an inhibitor and retarder blend comprising:

(A) at least one aromatic sulfonic acid;
(B) at least one amine;
(C) at least one nitrophenol; and
(D) at least one member of the group consisting of nitroxy radical-containing compounds and C-nitrosoanilines.

Aromatic sulfonic acids that can be employed in the practice of the present invention include, but are not limited to, those described in U.S. Published Application No. 2004/0147797, i.e., compounds of the structure:

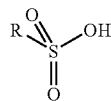

wherein R represents an alkylphenyl or an alkylnaphthyl group each having at least one straight or branched chain alkyl group having 1-32 carbon atoms, for example, toluenesulfonic acid, xylenesulfonic acid, cumenesulfonic acid, dodecylbenzenesulfonic acid, pentadecylbenzenesulfonic acid, dinonylnaphthalenesulfonic acid, and the like.

Preferably, R is an alkylphenyl group having at least one straight chain or branched chain alkyl of from 1 to 18 carbon atoms including, but not limited to, methyl, ethyl, propyl, butyl, pentyl, hexyl, heptyl, octyl, 2-ethyl hexyl, nonyl, decyl, undecyl, dodecyl, tridecyl, tetradecyl, pentadecyl, hexadecyl, heptadecyl, octadecyl, isomers of the foregoing, and the like; or cyclic alkyl groups, such as cyclopentyl, cyclohexyl, cycloheptyl, cyclooctyl, and cyclododecyl.

Amines that can be employed in the practice of the present invention include, but are not limited to, primary, secondary, or tertiary amines, and can comprise alkyl groups, aryl groups, or combinations thereof. Such amines include, but are not limited to, N-methyl-2-pyrrolidinone, α-naphthylamine, thiodiarylamines, p-phenylenediamine, o-phenylenediamine, 2,4-diamino diphenylamine, cyclohexyl naphthyl amine, polybutyl amines, methyl aniline, diphenyl-p-phenylene diamine, phenyl-(3-naphthylamine, isopropoxy-diphenylamine, aldol-α-naphthyl amine, symmetrical di-β-naphthyl-p-phenylenediamine, trimethyl dihydroquinoline, ditolylamines, phenyla-naphthylamine, phenyl-β-naphthylamine, diaminophenol, 4-cyclohexylaminophenol, p-aminophenol, o-aminophenol, 5-amino-2-hydroxytoluene, and the like.

Nitrophenols that can be employed in the practice of the present invention include, but are not limited to, 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrophenol, 2,4-dinitro-6-sec-butylphenol, 4-cyano-2-nitrophenol, 3-iodo-4-cyano-5-nitrophenol, m-nitro-p-cresol, 2,6-dinitro-p-cresol, and the like. 2,4-Dinitro-6-sec-butylphenol is preferred.

The nitroxyl radical-containing compounds that can be employed in the practice of the present invention are preferably stable hindered nitroxyl compounds having the structural formula:

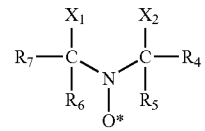

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl; and $X_1$ and $X_2$ (1) are independently selected from the group consisting of halogen, cyano, —COOR$_{10}$, —S—COR$_{10}$, —OCOR$_{10}$, (wherein $R_{10}$ is alkyl or aryl), amido, —S—C$_6$H$_5$, carbonyl, alkenyl, or alkyl of 1 to 15 carbon atoms, or (2) taken together, form a ring structure with the nitrogen.

In a particularly preferred embodiment, the stable hindered nitroxyl compound has the structural formula:

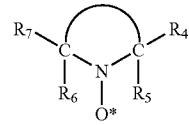

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl, and the

portion represents the atoms necessary to form a five-, six-, or seven-membered heterocyclic ring.

Accordingly, one of the several classes of cyclic nitroxides that can be employed in the practice of the present invention can be represented by the following structural formula:

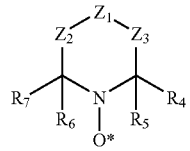

wherein $Z_1$, $Z_2$, and $Z_3$ are independently selected from the group consisting of oxygen, sulfur, secondary amines, tertiary amines, phosphorus of various oxidation states, and substituted or unsubstituted carbon atoms, such as >$CH_2$, >$CHCH_3$, >$C$=$O$, >$C(CH_3)_2$, >$CHBr$, >$CHCl$, >$CHI$, >$CHF$, >$CHOH$, >$CHCN$, >$C(OH)CN$, >$CHCOOH$, >$CHCOOCH_3$, >$CHCOOC_2H_5$, >$C(OH)COOC_2H_5$, >$C(OH)COOCH_3$, >$C(OH)CHOHC_2H_5$, >$CR_8OR_9$, >$CHNR_8R_9$, >$CCONR_8R_9$, >$C$=$NOH$, >$C$=$CH$—$C_6H_5$, >$CF_2$, >$CCl_2$, >$CBr_2$, >$CI_2$, >$CR_8PR_{13}R_{14}R_{15}$, and the like, where $R_8$ and $R_9$ are independently selected from the group consisting of hydrogen, alkyl, aryl, and acyl and $R_{13}$, $R_{14}$, and $R_{15}$ are independently selected from the group consisting of unshared electrons, alkyl, aryl, =$O$, $OR_{16}$, and $NR_{17}R_{18}$, where $R_{16}$, $R_{17}$, and $R_{18}$ are independently selected from the group consisting of hydrogen, alkyl, and aryl. Where $R_8$ and/or $R_9$ are alkyl, it is preferred that they be a lower alkyl (i.e., one having one to five carbon atoms, e.g., methyl, ethyl, propyl, butyl, pentyl, and isomers thereof).

Where $R_8$ and/or $R_9$ are aryl, it is preferred that they be aryl of from 6 to 10 carbon atoms, e.g., phenyl or naphthyl, which, in addition, may be substituted with non-interfering substituents, e.g., lower alkyl groups, halogens, and the like.

Where $R_8$ and/or $R_9$ are acyl, it is preferred that they be acyl of the structure

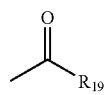

where $R_{19}$ is alkyl, aryl, $OR_{20}$, or $NR_{20}R_{21}$ and where $R_{20}$ and $R_{21}$ are alkyl, aryl, or

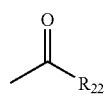

where $R_{22}$ is alkyl or aryl. Where $R_{19}$, $R_{20}$, $R_{21}$, or $R_{22}$ are alkyl, they are preferably alkyl of from 1 to 15 carbon atoms, more preferably lower alkyl of from 1 to 5 carbon atoms, as described above. Where $R_{19}$, $R_{20}$, $R_{21}$, or $R_{22}$ are aryl, they are preferably aryl of from 6 to 10 carbon atoms, as described above.

Another of the several classes of cyclic nitroxides that can be employed in the practice of the present invention can be represented by the following structural formula:

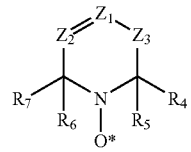

wherein $Z_1$ and $Z_2$, which may be the same or different, are nitrogen or substituted or unsubstituted carbon atoms, such as =$C(H)$—, =$C(CH_3)$—, =$C(COOH)$—, =$C(COOCH_3)$—, =$C(COOC_2H_5)$—, =$C(OH)$—, =$C(CN)$—, =$C(NR_8R_9)$—, =$C(CONR_8R_9)$—, and the like, and where $Z_3$, $R_8$, and $R_9$ are as described above.

The cyclic nitroxides employed in the practice of the present invention can also be derived from five-membered rings. These compounds are of the structure:

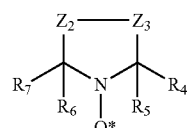

wherein $Z_2$ and $Z_3$, which may be the same or different, are sulfur, oxygen, secondary amines, tertiary amines, phosphorus of various oxidation states, or substituted or unsubstituted carbon atoms, such as, >$CH_2$, >$CHCH_3$, >$C$=$O$, >$C(CH_3)_2$, >$CHBr$, >$CHCl$, >$CHI$, >$CHF$, >$CHOH$, >$CHCN$, >$C(OH)CN$, >$CHCOOH$, >$CHCOOCH_3$, >$CHCOOC_2H_5$, >$C(OH)COOC_2H_5$, >$C(OH)COOCH_3$, >$C(OH)CHOHC_2H_5$, >$CR_8OR_9$, >$CHNR_8R_9$, >$CCONR_8R_9$, >$C$=$NOH$, >$C$=$CH$—$C_6H_5$, $CF_2$, $CCl_2$, $CBr_2$, $CI_2$, >$CR_8PR_{13}R_{14}R_{15}$, and the like, wherein the several R groups are as described above.

The cyclic nitroxides employed in the practice of the present invention can also have the structure:

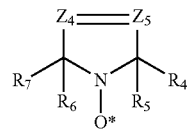

wherein $Z_4$ and $Z_5$, which can be the same or different, can be nitrogen or a substituted or unsubstituted carbon atom, such as =$C(H)$—, =$C(CH_3)$—, =$C(COOH)$—, =$C(COOCH_3)$—, =$C(COOC_2H_5)$—, =$C(OH)$—, =$C(CN)$—, =$C(NR_8R_9)$—, =$C(CONR_8R_9)$—, and the like, where $R_8$ and $R_9$ are as described above.

Another class of cyclic nitroxides that can be employed in the practice of the present invention is of the structure:

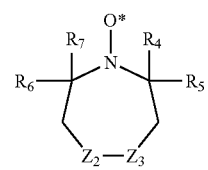

wherein $Z_2$ and $Z_3$, which may be the same or different, are sulfur, oxygen, secondary amines, tertiary amines, or substituted or unsubstituted carbon atoms, such as, >$CH_2$, >$CHCH_3$, >C=O, >$C(CH_3)_2$, >CHBr, >CHCl, >CHI, >CHF, >CHOH, >CHCN, >C(OH)CN, >CHCOOH, >$CHCOOCH_3$, >$CHCOOC_2H_5$, >$C(OH)COOC_2H_5$, >$C(OH)COOCH_3$, >$C(OH)CHOHC_2H_5$, >$CHNR_8R_9$, >$CCONR_8R_9$, >$CR_8OR_9$, >C=NOH, >C=CH—$C_6H_5$, $CF_2$, $CCl_2$, $CBr_2$, $Cl_2$, >$CR_8PR_{13}R_{14}R_{15}$, and the like, where the several R groups are as described above.

Further, two or more nitroxyl groups can be present in the same molecule, for example, by being linked through one or more of the Z-type moieties by a linking group E, as disclosed in U.S. Pat. No. 5,254,760, which is incorporated herein by reference.

As stated above, for all the nitroxyl structures above, $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl. The alkyl (or heteroatom-substituted alkyl) groups $R_4$ through $R_7$ can be the same or different and preferably contain 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethyl-hexyl, and the like. It is more preferred that $R_4$ through $R_7$ be independently selected lower alkyl (or heteroatom-substituted lower alkyl) of one to five carbon atoms (e.g., methyl, ethyl, propyl, butyl, pentyl, and isomers thereof). Where heteroatom substituents are present, they can, for example, include halogen, oxygen, sulfur, nitrogen, and the like. It is most preferred that all of $R_4$ through $R_7$ be methyl.

Examples of suitable nitroxide free radical compounds that can be used in combination with the sulfonated nitrophenols in the practice of the present invention, include, but are not limited to:

N,N-di-tert-butylnitroxide;
N,N-di-tert-amylnitroxide;
N-tert-butyl-2-methyl-1-phenyl-propylnitroxide;
N-tert-butyl-1-diethylphosphono-2,2-dimethylpropylnitroxide;
2,2,6,6-tetramethyl-piperidinyloxy;
4-amino-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;
4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetramethyl-1,2,5,6-tetrahydropyridine-1-oxyl;
4-carboxy-2,2,6,6-tetramethyl-1,2,5,6-tetrahydropyridine-1-oxyl;
4-carbomethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;
4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;
3-keto-4-oximino-2,2,5,5-tetramethylpyrrolidinyloxy;
3-keto-4-benzylidine-2,2,5,5-tetramethylpyrrolidinyloxy;
3-keto-4,4-dibromo-2,2,5,5-tetramethylpyrrolidinyloxy;
2,2,3,3,5,5-hexamethylpyrrolidinyloxy;
3-carboximido-2,2,5,5-tetramethylpyrrolidinyloxy;
3-oximino-2,2,5,5-tetramethylpyrrolidinyloxy;
3-hydroxy-2,2,5,5-tetramethylpyrrolidinyloxy;
3-cyano-3-hydroxy-2,2,5,5-tetramethylpyrrolidinyloxy;
3-carbomethoxy-3-hydroxy-2,2,5,5-tetramethylpyrrolidinyloxy;
3-carbethoxy-3-hydroxy-2,2,5,5-tetramethylpyrrolidinyloxy;
2,2,5,5-tetramethyl-3-carboxamido-2,5-dihydropyrrole-1-oxyl;
2,2,5,5-tetramethyl-3-amino-2,5-dihydropyrrole-1-oxyl;
2,2,5,5-tetramethyl-3-carbethoxy-2,5-dihydropyrrole-1-oxyl;
2,2,5,5-tetramethyl-3-cyano-2,5-dihydropyrrole-1-oxyl;
bis(1-oxyl-2,2,6,6-tetramethylpiperidin-4-yl)succinate;
bis(1-oxyl-2,2,6,6-tetramethylpiperidin-4-yl)adipate;
bis(1-oxyl-2,2,6,6-tetramethylpiperidin-4-yl)sebacate;
bis(1-oxyl-2,2,6,6-tetramethylpiperidin-4-yl)n-butylmalonate;
bis(1-oxyl-2,2,6,6-tetramethylpiperidin-4-yl)phthalate;
bis(1-oxyl-2,2,6,6-tetramethylpiperidin-4-yl)isophthalate;
bis(1-oxyl-2,2,6,6-tetramethylpiperidin-4-yl)terephthalate;
bis(1-oxyl-2,2,6,6-tetramethylpiperidin-4-yl)hexahydroterephthalate;
N,N'-bis(1-oxyl-2,2,6,6-tetramethylpiperidin-4-yl)adipamide;
N-(1-oxyl-2,2,6,6-tetramethylpiperidin-4-yl)-caprolactam;
N-(1-oxyl-2,2,6,6-tetramethylpiperidin-4-yl)-dodecylsuccinimide;
2,4,6-tris-[N-butyl-N-(1-oxyl-2,2,6,6-tetramethylpiperidin-4-yl)]-s-triazine;
4,4'-ethylenebis(1-oxyl-2,2,6,6-tetramethylpiperazin-3-one); and the like.

As used herein, the abbreviation TEMPO stands for 2,2,6,6-tetramethyl-1-piperidinyloxy. Thus, 4-amino-TEMPO is 4-amino-2,2,6,6-tetramethyl-1-piperidinyloxy; 4-hydroxy-TEMPO is 4-hydroxy-2,2,6,6-tetramethyl-1-piperidinyloxy (also known in the art as HTEMPO); 4-oxo-TEMPO is 4-oxo-2,2,6,6-tetramethyl-1-piperidinyloxy; and so on.

It is preferred that one member of a combination employed in the practice of the present invention be 4-amino-TEMPO, 4-oxo-TEMPO, 4-hydroxy-TEMPO, or TEMPO. Most preferred is 4-oxo-TEMPO.

Blends of two or more of the foregoing, e.g., 4-amino-TEMPO and 4-oxo-TEMPO, can also be employed.

Such stable nitroxide free radical compounds can be prepared by known methods. (See, for example, U.S. Pat. Nos. 3,163,677; 3,334,103; 3,372,182; 3,422,144; 3,494,930; 3,502,692; 3,873,564; 3,966,711; and 4,665,185; which are incorporated herein by reference.) They are suitable for use over a wide range of temperatures, but distillation temperatures employed with the ethylenically unsaturated monomers that are stabilized by the process of the present invention typically range from about 60° C. to about 180° C., preferably from about 70° C. to about 165° C., and, more preferably, from about 80° C. to about 150° C. Such distillations are generally performed at an absolute pressure in the range of about 10 to about 1,200 mm of Hg.

Where the inhibiting system of the present invention comprises a nitrosoaniline, it is preferably one having the structure:

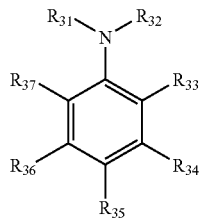

wherein $R_{31}$ and $R_{32}$ are independently selected from the group consisting of hydrogen, alkyl, aryl, acyl, hydroxyl, alkoxy, nitroso, and sulfonyl, or $R_{31}$ and $R_{32}$ can form a cyclic ring that is aryl, cycloalkyl, polyaryl, or heterocyclic;

$R_{33}$ through $R_{37}$ are independently selected from the group consisting of hydrogen, alkyl, aryl, acyl, hydroxyl, alkoxy, acyloxy, $NR_{38}(R_{39})$, nitro, nitroso, halogen, and sulfonyl, or any two adjacent R's can form a cyclic ring that is aryl, cycloalkyl, polyaryl, or heterocyclic, provided that at least one of $R_{33}$ through $R_{37}$ must be a nitroso group; and $R_{38}$ and $R_{39}$ are independently selected from the group consisting of hydrogen, alkyl, aryl, acyl, and nitroso. Preferably $R_{38}$ is hydrogen and $R_{39}$ is alkyl.

It is preferred that the nitrosoaniline of the present invention be a C-nitrosoaniline. The most preferred nitrosoaniline for use in the practice of the present invention is 4-nitroso-N-(1,4-dimethylpentyl)-aniline.

Those skilled in the art will be aware that nitrosoaniline derivatives are understood to tautomerize to quinone imine oxime derivatives, i.e.,

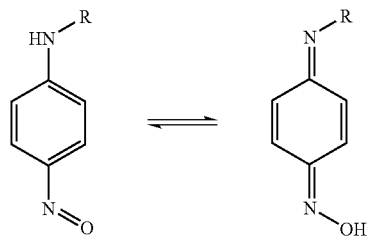

See, for example, Sidgwick, N. V., *The Organic Chemistry of Nitrogen*, Third Edition, Clarendon Press, Oxford, 1966. Thus, both forms can be present, especially in solution at elevated temperatures, and can be expected to contribute to the inhibiting activity of these compounds.

C-nitrosoaniline compounds can be prepared by C-nitrosation of the corresponding anilines in any typical manner used for the C-nitrosation of aromatic amines. For example, reaction of the amine with cold nitrous acid produces an N-nitroso compound that rearranges to a para-nitrosoaniline under the influence of an excess of hydrochloric acid. In some cases, it is more convenient to effect the nitrosation and rearrangement in one step by conducting the reaction in methanol solution in the presence of an excess of hydrogen chloride under anhydrous conditions. This procedure is described in U.S. Pat. No. 2,046,356.

The vinyl aromatic monomer, the premature polymerization and polymer growth of which is an object of the present invention, can be any such monomer for which unintended polymerization and/or polymer growth during its manufacture, storage, and/or distribution is a problem. Among those monomers that will benefit from the practice of the present invention are: styrene, α-methylstyrene, styrene sulfonic acid, vinyltoluene, divinylbenzenes, polyvinylbenzenes, alkylated styrene, 2-vinylpyridine, and the like.

The vinyl aromatic monomers will not necessarily be stabilized indefinitely by the presence of the inhibitor(s), especially when the monomers are heated as in distillation, but they can be considered to be stabilized as long as A) there is a measurable increase in the time for which they can be heated before the onset of polymerization and/or polymer growth in a static system, B) the amount of polymer made at a constant temperature remains constant over time in a dynamic system, and/or C) the rate of polymer growth is significantly slower than when the growth inhibiting system is not present.

Those skilled in the art will understand that, if desired, free radical scavengers can also be included in the practice of the present invention. For example, air or $O_2$, as disclosed in U.S. Pat. Nos. 5,545,782 and 5,545,786, can be added, as can the aromatic nitro compounds disclosed in U.S. Pat. No. 5,254,760, the dihetero-substituted benzene compounds having at least one transferable hydrogen, e.g., a quinone derivative such as the mono-methyl-ether of hydroquinone disclosed in European Patent Application 0 765 856 A1, the iron compounds disclosed in WO 98/25872, and other inhibitors, e.g., phenolics and certain inorganic salts, well-known to those skilled in the art.

The polymerization inhibitors can be introduced into the monomer to be protected by any conventional method. They can, for example, be added as a concentrated solution in suitable solvents just upstream from the point of desired application by any suitable means. In addition, individual inhibiting components can be injected separately into the distillation train along with the incoming feed and/or through separate and multiple entry points, provided there is an efficient distribution of the inhibiting composition. Since the inhibitors are gradually depleted during the distillation operation, it is generally advantageous to maintain the appropriate amount of them in the distillation apparatus by adding them during the course of the distillation process. Adding inhibitors can be done either on a generally continuous basis or intermittently, in order to maintain the inhibitor concentration above the minimum required level.

The total inhibitor concentration should be from about 1 to about 1000 ppm versus the monomer being inhibited; preferably from about 100 to about 1000 ppm, depending on the conditions of use. The aromatic sulfonic acid is preferably present in a range of from about 1 to about 500 ppm, more preferably from about 50 to about 500 ppm; the amine is preferably present in a range of from about 1 to about 200 ppm, more preferably from about 5 to about 100 ppm; the nitroxy radical type compound is preferably present in a range of from about 1 to about 200 ppm, more preferably from about 5 to about 150 ppm; the nitrosoaniline is preferably present in a range of from about 1 to about 200 ppm, more preferably from about 5 to about 150 ppm; and the nitrophenol is preferably present in a range of from about 1 to about 500 ppm, more preferably from about 50 to about 500 ppm.

The advantages and the important features of the present invention will be more apparent from the following examples.

EXAMPLES

Example 1

The styrene inhibitor and retarder properties of the claimed combinations were tested in a Continuous Dynamic Reboiler Test monitoring the polymer formation with UV spectrophotometry. According to this test, the inhibitor is added to styrene monomer from which tert-butylcatechol (TBC) is previously removed by distillation. A quantity of 180 grams of this styrene is loaded into a flask, which is immersed into an oil bath. The temperature of styrene is usually 116° C. During the test, a fresh feed is charged into the flask at the rate of three grams/minute and, at the same time, the material from the flask is discharged at the same rate. The steady stage is continued until equilibrium. For the feed shut off stage, the charging and discharging are discontinued. Samples are taken every hour at the steady stage and every five to ten minutes at feed shut off.

The Continuous Dynamic Reboiler Test of the combination of 4-oxo-TEMPO/DBSA/NMP/DNBP at concentrations of 100 ppm/100 ppm/30 ppm/250 ppm, respectively, resulted in 0.0004% polymer in five hours steady stage and 0.31% polymer after two hours feed shut off.

Example 2

The Continuous Dynamic Reboiler Test of the combination of 4-oxo-TEMPO/DBSA/NMP/DNBP at concentrations of 100 ppm/250 ppm/75 ppm/250 ppm, respectively, resulted in 0.0004% polymer in five hours steady stage and 0.157% polymer after two hours feed shut off.

Example 3

The Continuous Dynamic Reboiler Test of 4-nitroso-N-(1, 4-dimethylpentyl)-aniline/DBSA/NMP/DNBP at concentrations of 100 ppm/250 ppm/75 ppm/250 ppm, respectively, resulted in 0.002% polymer in five hours steady stage and 0.007% polymer after two hours feed shut off.

In view of the many changes and modifications that can be made without departing from principles underlying the invention, reference should be made to the appended claims for an understanding of the scope of the protection to be afforded the invention.

What is claimed is:

1. A composition comprising a blend of:
   (A) from about 50 ppm to about 500 ppm by weight, based on the weight of the monomers, of at least one aromatic sulfonic acid;
   (B) at least one amine;
   (C) at least one nitrophenol; and
   (D) at least one member of the group consisting of nitroxy radical-containing compounds and C-nitrosoanilines.

2. The composition of claim 1 wherein the aromatic sulfonic acid is a compound of the structure:

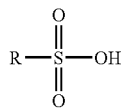

wherein R represents an alkylphenyl or an alkylnaphthyl group each having at least one straight or branched chain alkyl group having 1-32 carbon atoms.

3. The composition of claim 1 wherein the amine is selected from the group consisting of N-methyl-2-pyrrolidinone, α-naphthylamine, thiodiarylamines, p-phenylenediamine, o-phenylenediamine, 2,4-diamino diphenylamine, cyclohexyl naphthyl amine, polybutyl amines, methyl aniline, diphenyl-p-phenylene diamine, phenyl-β-naphthylamine, isopropoxydiphenylamine, aldol-α-naphthyl amine, symmetrical di-β-naphthyl-p-phenylenediamine, trimethyl dihydroquinoline, ditolylamines, phenyl-α-naphthylamine, phenyl-β-naphthylamine, diaminophenol, 4-cyclohexylaminophenol, p-aminophenol, o-aminophenol, and 5-amino-2-hydroxytoluene.

4. The composition of claim 1 wherein the nitrophenol is selected from the group consisting of 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrophenol, 2,4-dinitro-6-sec-butylphenol, 4-cyano-2-nitrophenol, 3-iodo-4-cyano-5-nitrophenol, m-nitro-p-cresol, and 2,6-dinitro-p-cresol.

5. The composition of claim 1 wherein (D) is a stable hindered nitroxyl compound having the structural formula:

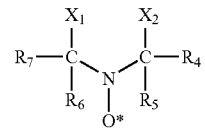

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl; and $X_1$ and $X_2$ (1) are independently selected from the group consisting of halogen, cyano, —COOR$_{10}$, —S—COR$_{10}$, —OCOR$_{10}$, (wherein $R_{10}$ is alkyl or aryl), amino, —S—C$_6$H$_5$, carbonyl, alkenyl, or alkyl of 1 to 15 carbon atoms, or (2) taken together, form a ring structure with the nitrogen.

6. The composition of claim 1 wherein (D) is a nitrosoaniline having the structure:

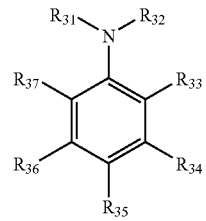

wherein either
   (i) $R_{31}$, and $R_{32}$ are independently selected from the group consisting of hydrogen, alkyl, aryl, acyl, hydroxyl, alkoxy, nitroso, and sulfonyl, or
   (ii) $R_{31}$ and $R_{32}$ can form a cyclic ring that is aryl, cycloalkyl, polyaryl, or heterocyclic; and
wherein either
   (i) $R_{33}$ through $R_{37}$ are independently selected from the group consisting of hydrogen, alkyl, aryl, acyl, hydroxyl, alkoxy, acyloxy, NR$_{38}$(R$_{39}$), nitro, nitroso, halogen, and sulfonyl, provided that at least one of $R_{33}$ through $R_{37}$ must be a nitroso group, or (ii) any two adjacent R's can form a cyclic ring that is aryl, cycloalkyl, polyaryl, or heterocyclic, provided that at least one of $R_{33}$ through $R_{37}$ must be a nitroso group; and $R_{38}$ and $R_{39}$ are independently selected from the group consisting of hydrogen, alkyl, aryl, acyl, and nitroso.

7. A composition comprising a vinyl aromatic monomer and a polymerization inhibiting and retarding amount of a blend comprising:

(A) from about 50 ppm to about 500 ppm by weight, based on the weight of the monomers, of at least one aromatic sulfonic acid;

(B) at least one amine;

(C) at least one nitrophenol; and (D) at least one member of the group consisting of nitroxy radical-containing compounds and C-nitrosoanilines.

8. The composition of claim 7 wherein the aromatic sulfonic acid is a compound of the structure:

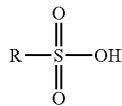

wherein R represents an alkylphenyl or an alkylnaphthyl group each having at least one straight or branched chain alkyl group having 1-32 carbon atoms.

9. The composition of claim 7 wherein the amine is selected from the group consisting of N-methyl-2-pyrrolidinone, α-naphthylamine, thiodiarylamines, p-phenylenediamine, o-phenylenediamine, 2,4-diamino diphenylamine, cyclohexyl naphthyl amine, polybutyl amines, methyl aniline, diphenyl-p-phenylene diamine, phenyl-β-naphthylamine, isopropoxydiphenylamine, aldol-α-naphthyl amine, symmetrical di-β-naphthyl-p-phenylenediamine, trimethyl dihydroquinoline, ditolylamines, phenyl-α-naphthylamine, phenyl-β-naphthylamine, diaminophenol, 4-cyclohexylaminophenol, p-aminophenol, o-aminophenol, and 5-amino-2-hydroxytoluene.

10. The composition of claim 7 wherein the nitrophenol is selected from the group consisting of 2,6-dinitro-4-methylphenol, 2-nitro-4-methylphenol, 2,4-dinitro-1-naphthol, 2,4,6-trinitrophenol (picric acid), 2,4-dinitro-6-methylphenol, 2,4-dinitrophenol, 2,4-dinitro-6-sec-butylphenol, 4-cyano-2-nitrophenol, 3-iodo-4-cyano-5-nitrophenol, m-nitro-p-cresol, and 2,6-dinitro-p-cresol.

11. The composition of claim 7 wherein (D) is a stable hindered nitroxyl compound having the structural formula:

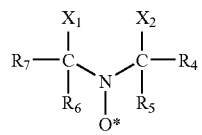

wherein $R_4$ and $R_7$ are independently selected from the group consisting of hydrogen, alkyl, and heteroatom-substituted alkyl and $R_5$ and $R_6$ are independently selected from the group consisting of alkyl and heteroatom-substituted alkyl; and $X_1$ and $X_2$ (1) are independently selected from the group consisting of halogen, cyano, —$COOR_{10}$, —S—$COR_{10}$, —$OCOR_{10}$, (wherein $R_{10}$ is alkyl or aryl), amido, —S—$C_6H_5$, carbonyl, alkenyl, or alkyl of 1 to 15 carbon atoms, or (2) taken together, form a ring structure with the nitrogen.

12. The composition of claim 7 wherein (D) is a nitrosoaniline having the structure:

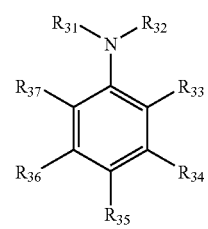

wherein either (i) $R_{31}$, and $R_{32}$ are independently selected from the group consisting of hydrogen, alkyl, aryl, acyl, hydroxyl, alkoxy, nitroso, and sulfonyl, or (ii) $R_{31}$ and $R_{32}$ can form a cyclic ring that is aryl, cycloalkyl, polyaryl, or heterocyclic; and wherein either (i) $R_{33}$ through $R_{37}$ are independently selected from the group consisting of hydrogen, alkyl, aryl, acyl, hydroxyl, alkoxy, acyloxy, $NR_{38}(R_{39})$, nitro, nitroso, halogen, and sulfonyl, provided that at least one of $R_{33}$ through $R_{37}$ must be a nitroso group, or (ii) any two adjacent R's can form a cyclic ring that is aryl, cycloalkyl, polyaryl, or heterocyclic, provided that at least one of $R_{33}$ through $R_{37}$ must be a nitroso group; and $R_{38}$ and $R_{39}$ are independently selected from the group consisting of hydrogen, alkyl, aryl, acyl, and nitroso.

13. The composition of claim 1 wherein (A) is dodecylbenzenesulfonic acid, (B) is N-methyl-2-pyrrolidinone, (C) is 2,4-dinitro-6-sec-butylphenol, and (D) is 4-oxo-2,2,6,6-tetramethyl-1-piperidinyloxy or 4-nitroso-N-(1,4-dimethylpentyl)-aniline.

14. The composition of claim 7 wherein (A) is dodecylbenzenesulfonic acid, (B) is N-methyl-2-pyrrolidinone, (C) is 2,4-dinitro-6-sec-butylphenol, and (D) is 4-oxo-2,2,6,6-tetramethyl-1-piperidinyloxy or 4-nitroso-N-(1,4-dimethylpentyl)-aniline.

* * * * *